United States Patent [19]

Schneider

[11] Patent Number: 5,657,763
[45] Date of Patent: Aug. 19, 1997

[54] ELECTRIC REFLEX HAMMER

[75] Inventor: Robert L. Schneider, Middleton, Wis.

[73] Assignee: Nicolet Biomedical, Inc., Madison, Wis.

[21] Appl. No.: 436,834

[22] Filed: May 8, 1995

[51] Int. Cl.⁶ .................................................. A61B 19/00
[52] U.S. Cl. ........................................ 128/740; 128/774
[58] Field of Search .................................. 128/733, 740, 128/739, 744, 55, 54; 327/3; 307/112

[56] References Cited

U.S. PATENT DOCUMENTS

| | | | |
|---|---|---|---|
| 3,185,146 | 5/1965 | Leopoldi | 128/740 |
| 4,737,660 | 4/1988 | Allen et al. | 307/112 |
| 4,759,377 | 7/1988 | Dykstra | 128/733 |

OTHER PUBLICATIONS

Nicolet Biomedical Instruments, Drawing, HRDW/Tendon Hammer, May 30, 1989.

Primary Examiner—Sam Rimell
Assistant Examiner—Pamela L. Wingood
Attorney, Agent, or Firm—Foley & Lardner

[57] ABSTRACT

An electric reflex hammer is provided which produces consistent triggering signals at the moment of impact of the hammer against a patient. A sealed switch, rigidly attached to the hammer near the striking surface of the hammer, and a switch activator, used to make the switch closure, provide the triggering signal. Use of the sealed switch allows the switch contacts to move freely without the tension or weight effects of connection wires attached to the contacts. Instead, fixed terminals extending from the sealed switch are provided, whereby the hammer may be attached by a wire to an electrical measuring device. Consistent switch closure and triggering signals are achieved, therefore, regardless of how the connection wire is attached to the hammer, or how the switch is activated. This improvement in consistency allows for much more accurate measurement of muscle response time using electronic measurement of physiological signals, such as through use of an evoked potential recording device.

11 Claims, 3 Drawing Sheets

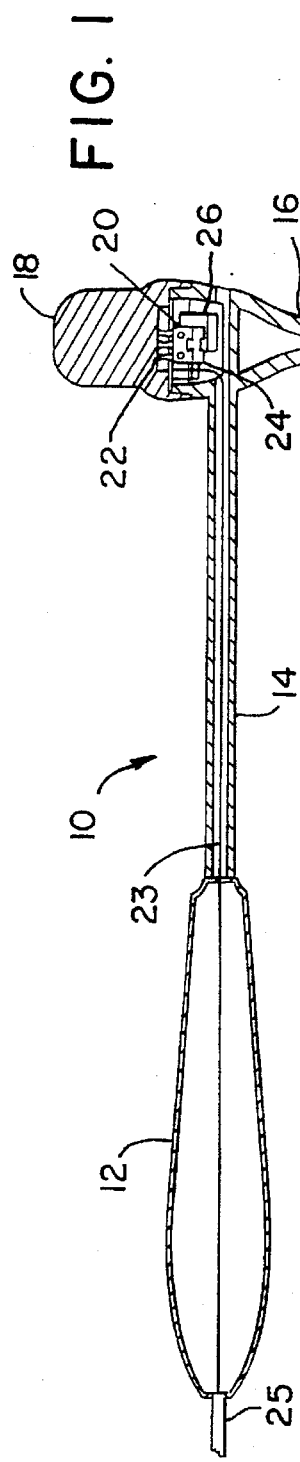
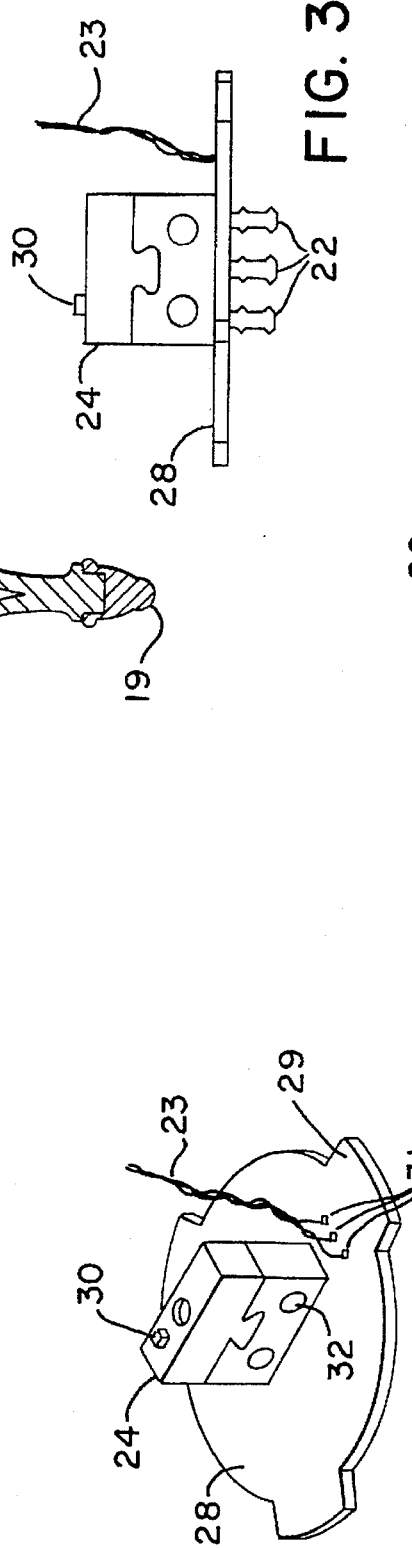
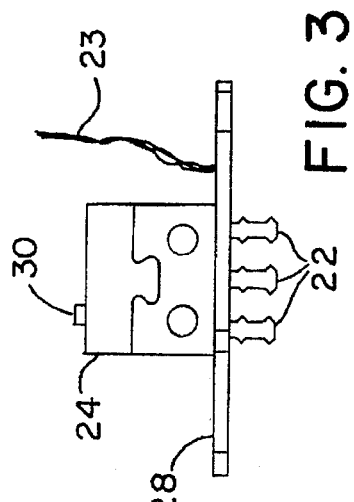
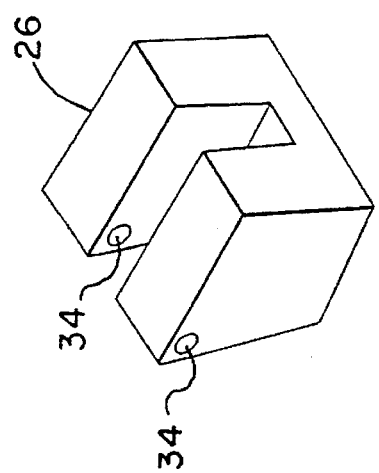

5,657,763

ELECTRIC REFLEX HAMMER

FIELD OF THE INVENTION

This invention pertains generally to the field of reflex hammers used by physicians to check the muscle response of patients, and particularly to electric reflex hammers having the capability to provide an electrical signal at the moment of impact of the hammer against a patient.

BACKGROUND OF THE INVENTION

Reflex hammers, also known as tendon hammers, are used by physicians to check the reflex, or muscle response, of patients. The traditional reflex hammer consists of a shaft with a handle at one end and a hammer head at the other end of the shaft. The head has a striking surface, typically made of hard rubber. A physician checks a patient's muscle response by striking the hard rubber end of the reflex hammer against the patient's body, typically at the knee, elbow, or forehead. The physician then visually checks for the reflex muscle response to the strike.

More advanced reflex hammers have an electronic triggering mechanism in the head of the hammer. The triggering mechanism provides an electrical signal at the time of impact. This electrical signal can be provided to a device for measuring the reflex response to the strike. In this way a quantifiable, versus visual, response may be obtained. For example, an electric reflex hammer may be used when a patient undergoes a diagnostic procedure involving an evoked potential (EP) recording. The electric reflex hammer provides a signal to the EP recorder at the moment of impact of the hammer against the patient. The EP recorder can then correlate the time of impact with changes that may occur in the physiological signals that the EP recorder is recording from the patient.

Electric reflex hammers typically contain a momentary contact switching mechanism that opens or closes when the hammer strikes the patient. This switching mechanism typically comprises two or more contacts activated by a spring mechanism. A wire extends from one of the contacts for connection of the reflex hammer to the electric measuring device. A second wire, also for connection to the measuring device, is attached to a second contact at the end of a spring. On impact of the hammer head with a patient, the spring compresses and the two contacts mate, completing the circuit between the wires and providing a signal to the measuring device.

This type of triggering mechanism, however, often results in inconsistent contact closure time and, therefore, inconsistent triggering signals among otherwise identical reflex hammers. This inconsistency results from how the contact is attached to the spring and how the wire is attached to the contact on the spring. How the wires and contacts are attached affects the operation of the closure of the contacts in response to a hammer strike. Soldering of the wire and contact to the spring adds weight to the spring, which affects its motion in response to a strike. Since the solder weight among reflex hammers will vary, the contact closure response will also vary. Attaching the contact and wire to the spring by a screw or other connection mechanism also adds weight, affecting the response of the spring. Additionally, the spring and the wires attached to the spring have a degree of tension. When the spring tries to compress in response to a strike this tension restricts the compression, thereby affecting the closure of the contacts. The combined effects of additional and inconsistent weight resulting from the way the contact and wire are connected to the spring, and the tension in the wire and spring itself, makes the contact closure inconsistent. This inconsistency affects the measurement of the response time of muscles to a strike of the hammer.

SUMMARY OF THE INVENTION

In accordance with the present invention, an electric reflex hammer is provided which provides consistent triggering signals when the hammer strikes a patient. This objective of consistency is achieved by removing the complication of weight and tension away from the contact closure point of the hammer triggering mechanism. The triggering mechanism of the present invention includes a sealed switch attached to a rigid substrate which, in turn, is secured to the end of the hammer near the striking surface, and an activator which is used to make the switch closure. The actual electrical contacts, which are sealed inside the switch, are allowed to move freely, not being connected to any wires. Instead, fixed terminals are provided which extend from the sealed switch, to which wires connecting the electric reflex hammer to a measuring device may be attached. The electrical wires attached to the hammer, and the hinged activator, have no effect on the movement of the switch closure. This allows for consistent switch closure regardless of how the wires are attached or how the switch is activated. This improvement in consistency allows much more accurate measurement of muscle response time to a strike by the reflex hammer.

Further objects, features and advantages will be apparent from the following detailed description when taken in conjunction with the accompanying drawings.

BRIEF DESCRIPTION OF THE DRAWINGS

In the drawings:

FIG. 1 is a side view, in cross section, of an electric reflex hammer in accordance with the present invention.

FIG. 2 is a perspective view of a sealed switch attached to a rigid substrate as employed in the reflex hammer of the present invention.

FIG. 3 is a side view of the sealed switch and rigid substrate of FIG. 2.

FIG. 4 is a perspective view of a switch activator as employed in the reflex hammer of the present invention.

DETAILED DESCRIPTION OF THE INVENTION

Figure 5:
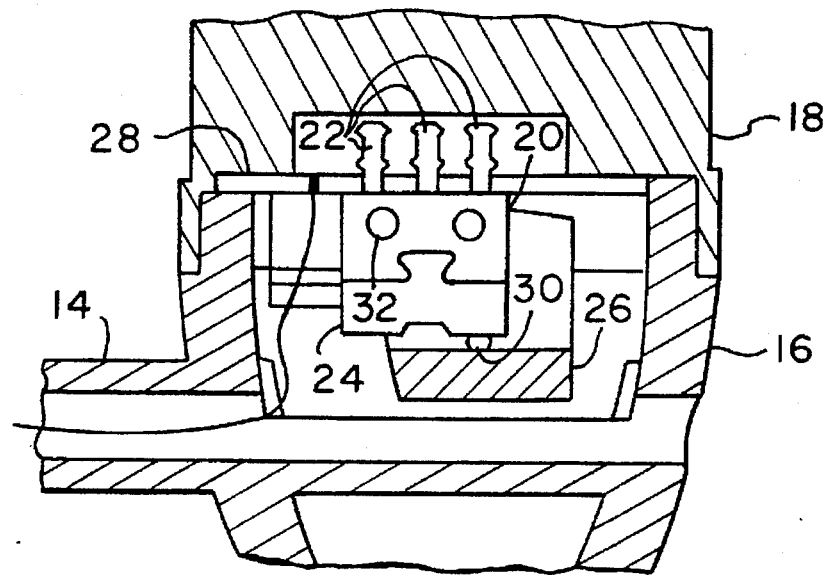
FIG. 5 is a detailed side view, in cross section, of a portion of the head and the triggering mechanism of an electric reflex hammer in accordance with the present invention.

An electric reflex hammer in accordance with the present invention is shown generally at 10 in FIG. 1. The reflex hammer 10 includes a handle 12, attached to a shaft 14, and a head 16 attached to the end of the shaft 14 opposite the handle 12. The handle 12, shaft 14, and head 16 of the hammer are also shown in the perspective view of FIG. 7. Attached to the head 16 is a striking surface structure 18, which is typically made of a material such as hard rubber.

The hammer 10 may also have a second striking surface structure 19 attached to the head 19, however, when the triggering mechanism described below is to be used the primary striking surface 18 is employed. These basic components of the hammer, the handle 12, shaft 14, head 16, and striking surfaces 18 and 19, may preferably be purchased as a single unit, such as the Model DE10716 hammer made by V. Mueller Co. of Germany. This unit has no electronics. Other similar units might also be used. In operation, a physician will grasp the handle 12 of the hammer 10 and strike the striking surface 18 against a patient, such as at the knee, elbow, or forehead, to evoke a muscle response.

An electric triggering mechanism 20 is attached to the shaft 14 near, or preferably as part of, the head 16. The triggering mechanism 20 includes two or more terminals 22 which may be attached by a wire 23 extending through a hollow bore through the shaft 14 and handle 12 to an electric measuring device such as an evoked potential (EP) recording device (not shown). The wire 23 may form a cable 25 which extends from the handle 12 and preferably terminates in a phono plug type connector for connection to the measuring device. The triggering mechanism closes or opens a circuit between the terminals 22 at the moment of impact of the strike surface 18 with a patient. In this manner, a signal is provided at the terminals 22 and on the wire 23 which indicates the strike time and which may be recorded by the measuring device and used to correlate the time of impact with a measured physiological response.

Figure 7:
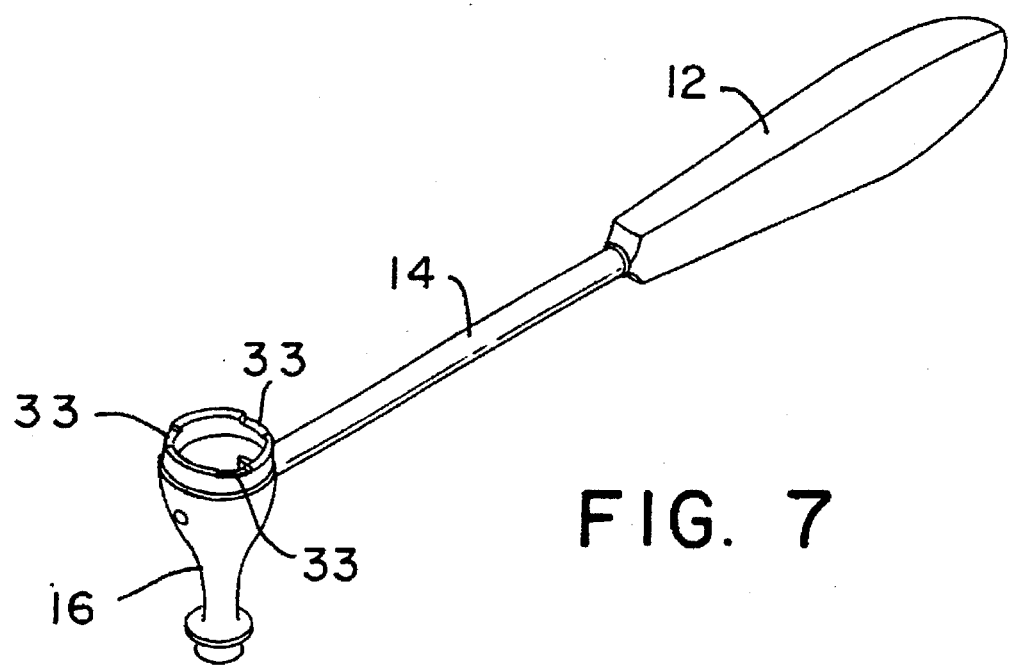
FIG. 7 is a perspective view of the handle, shaft, and head of an electric reflex hammer in accordance with the present invention.

The triggering mechanism 20 includes a commercial sealed switch 24 and an activator 26. A preferred switch is the Model US10D10A00 switch made by Microswitch, although other sealed switches may also be used. As shown in FIG. 2 and FIG. 3, the sealed switch 24 is secured to a rigid substrate 28. The substrate 28 preferably doubles as a circuit board. Conducting connections, not shown, deposited on the substrate 28 in a conventional manner connect the terminals 22 to connection points 31 on the substrate 28. These connection points 31 may preferably be holes through the substrate/circuit board 28 where three conductors from the wire 23 are attached to the substrate 28, such as by directly soldering to the substrate 28 or with a mechanical connection. In this manner, the wire 23 is connected to the terminals 22. The substrate 28 is then preferably securely attached to the shaft 14 or head 16 of the hammer 10 near the striking surface structure 18. For this purpose, tabs 29 are integrally formed extending from the substrate 28 which may be locked into grooves 33, shown in FIG. 7, provided in the head 26 of the hammer 10 adjacent to the striking surface structure 18.

The switch 24 has a switch closure button 30 which is used to complete or open a circuit between two of the fixed terminals 22 which extend from the switch 24 through the substrate 28. The third terminal is the chasis ground. Any exposed metal parts of the hammer 10 should be grounded to the chasis. The switch 24 shown in FIG. 2 is a button type switch; however, switches using other closure mechanisms, such as rocker type switches, may also be used. When the switch button 30 is depressed, an electrical connection is effected within the switch 24 between two of the terminals 22. For example, for the switch shown in FIG. 3, when the switch closure mechanism 30 is not depressed, an open circuit may exist between the terminals 22. At the moment of depression of the closure mechanism 30, an electrical connection between the terminals 22 is closed. As pressure on the switch closure mechanism 30 is removed, the closure mechanism 30 returns to its original position, re-opening the connection between the terminals 22. The closing and opening of the contacts within the switch 24 is not affected by the connection of wires to the terminals 22. The closing and opening of this connection results in a triggering signal at the terminals 22 which may be provided to a measuring device via the wires 23 attached to the terminals 22 of the substrate 28.

The activator 26 is used to activate the switch closure button 30 when the striking surface structure 18 impacts a patient. In the preferred embodiment of the invention presented, a hole 32 is provided in the switch 24 structure, and corresponding holes 34, as shown in the detailed view of the activator of FIG. 4, are provided in the activator 26 for attaching the activator 26 by a hinge pin or pins 36 in a pivoting relation to the switch 24. The activator 26 need not be hinged directly to the switch 24 but may be hinged, or otherwise movably attached, to the substrate 28 or to other structures attached to the substrate 28 or the head 16 or shaft 14 of the hammer 10. The activator 26 is preferably made of a heavy material such as cold rolled steel to increase the potential momentum of the activator 26.

Figure 6:
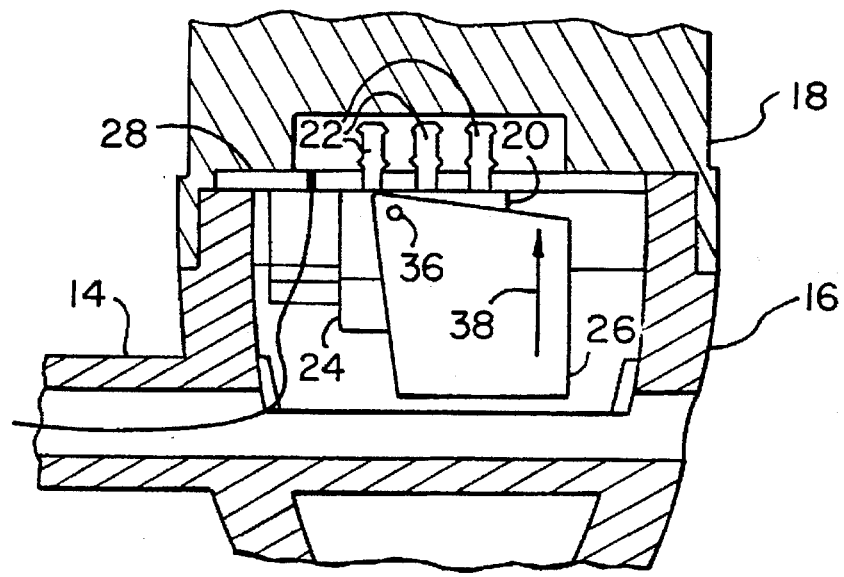
FIG. 6 is a detailed side view, in partial cross section, of a portion of the head of the reflex hammer, showing a side view of the triggering mechanism of FIG. 5.

The triggering mechanism 20 of the present invention is shown fully assembled, in the head 16 of a reflex hammer 10 in FIG. 5 and FIG. 6. The switch substrate/circuit board 28 is securely attached to the head 16 of the hammer 10. The activator 26 is attached to the switch 24 by a dowel hinge pin 36 extending through the hole 32 in the switch 24 and the holes 34 in the activator 26, so that the activator 26 may freely pivot about the pin 36. Note that the range of motion of the activator 26 is limited by the substrate 28.

As the physician begins a forward stroke with the hammer 10, the head 16, including the activator 26, accelerates in the direction indicated by the arrow 38. At the moment of impact of the striking surface structure 18 with the patient the head 16 comes to a sudden halt, momentum carries the activator 26 forward, rotating about the pin 36 in the direction indicated by arrow 38. The switch closure mechanism 30 is thereby closed, and a signal appears at the terminals 22 and on the wire 23. The signal on the wire 23 will consistently occur at almost the exact instant of impact of the striking surface structure 18 with the patient. Therefore, the time of impact can be correlated with the changes that may occur in physiological signals from the patient which are being measured by a measuring device to which the cable 25 from the hammer 10 is attached.

It is understood that the invention is not confined to the particular embodiment set forth herein as illustrative, but embraces such modified forms thereof as come within the scope of the following claims.

What is claimed is:

1. An electric reflex hammer, comprising:
   (a) a shaft having a first end and a second end;
   (b) a handle attached to the first end of the shaft;
   (c) a head attached to the second end of the shaft and having a striking surface; and
   (d) a triggering mechanism securely attached to the shaft near the head, the triggering mechanism comprising a sealed switch rigidly secured to the shaft and having at least two terminals and a switch closure mechanism to create an electrical connection between the terminals when the closure mechanism is activated, and a moveable activator attached by a hinge to the sealed switch such that when the head is accelerated toward a patient the moveable activator is accelerated and such that when the striking surface strikes a patient to rapidly decelerate the head of the reflex hammer the momentum of the activator causes the activator to rotate about the hinge to impact the switch closure mechanism to thereby activate the closure mechanism when the striking surface impacts the patient.

2. The electric reflex hammer of claim 1 wherein the striking surface is made of hard rubber.

3. The electric reflex hammer of claim 1 wherein the sealed switch is secured to a rigid substrate which is securely attached to the shaft near the head.

4. The electric reflex hammer of claim 3 wherein the rigid substrate is a circuit board having electrically conducting connections on a surface thereof extending between the terminals and a wire connection point on the substrate.

5. The electric reflex hammer of claim 4 additionally comprising a wire connected to the connection point and extending from the electric reflex hammer through a bore through the shaft and the handle.

6. The electric reflex hammer of claim 5 wherein the connection of the wire to the connection point is by soldering.

7. An electric reflex hammer, comprising:

(a) a shaft having a first end and a second end;

(b) a handle attached to the first end of the shaft;

(c) a head attached to the second end of the shaft and having a striking surface;

(d) a rigid substrate securely attached to the shaft near the head; and (e) a triggering mechanism securely attached to the rigid substrate, the triggering mechanism comprising a sealed switch secured to the substrate and having at least two terminals and a switch closure mechanism to create an electrical connection between the terminals when the closure mechanism is activated, and a moveable activator attached by a hinge to the switch such that when the head is accelerated toward a patient the moveable activator is accelerated and such that when the striking surface strikes a patient to rapidly decelerate the head of the reflex hammer the momentum of the activator causes the activator to rotate about the hinge in response to the impact of the striking surface on the patient to thereby activate the closure mechanism when the striking surface impacts the patient.

8. The electric reflex hammer of claim 7 wherein the striking surface is made of hard rubber.

9. The electric reflex hammer of claim 7 wherein the rigid substrate is a circuit board having electrically conducting connections on a surface thereof extending between the terminals and a wire connection point on the substrate.

10. The electric reflex hammer of claim 9 additionally comprising a wire connected to the connection point and extending from the electric reflex hammer through a bore through the shaft and the handle.

11. The electric reflex hammer of claim 10 wherein the connection of the wire to the connection point is by soldering.

* * * * *